(12) United States Patent
Putz

(10) Patent No.: US 8,439,714 B2
(45) Date of Patent: May 14, 2013

(54) ELECTRICAL CONNECTOR FOR AN IN-BODY MULTI-CONTACT MEDICAL ELECTRODE DEVICE

(75) Inventor: David A. Putz, Racine, WI (US)

(73) Assignee: Ad-Tech Medical Instrument Corp., Racine, WI (US)

( * ) Notice: Subject to any disclaimer, the term of this patent is extended or adjusted under 35 U.S.C. 154(b) by 281 days.

(21) Appl. No.: 12/956,729

(22) Filed: Nov. 30, 2010

(65) Prior Publication Data

US 2012/0135624 A1  May 31, 2012

(51) Int. Cl.
*H01R 9/24* (2006.01)
(52) U.S. Cl.
USPC .......................................... 439/891; 600/372
(58) Field of Classification Search .................. 439/866, 439/891, 682, 683, 79, 909; 600/372–374
See application file for complete search history.

(56) References Cited

U.S. PATENT DOCUMENTS

| | | | |
|---|---|---|---|
| 3,842,394 A | 10/1974 | Bolduc | |
| 3,951,154 A | 4/1976 | Hartlaub | |
| 4,735,208 A | 4/1988 | Wyler et al. | |
| 4,744,371 A | 5/1988 | Harris | |
| 4,805,625 A | 2/1989 | Wyler | |
| 4,903,702 A | 2/1990 | Putz | |
| 4,998,897 A | 3/1991 | Rose | |
| 5,044,368 A | 9/1991 | Putz | |
| 5,076,806 A | 12/1991 | Hotea et al. | |
| 5,097,835 A | 3/1992 | Putz | |
| 5,207,593 A | 5/1993 | Bogiel | |
| 5,560,358 A * | 10/1996 | Arnold et al. | 600/373 |
| 5,667,615 A | 9/1997 | Maurer et al. | |
| 5,766,042 A * | 6/1998 | Ries et al. | 439/668 |
| 5,843,141 A | 12/1998 | Bischoff et al. | |
| 6,415,168 B1 | 7/2002 | Putz | |
| 6,453,185 B1 | 9/2002 | O'Keefe | |
| 6,575,759 B1 | 6/2003 | Ollivier | |
| 6,671,534 B2 | 12/2003 | Putz | |
| 6,725,096 B2 | 4/2004 | Chinn et al. | |
| 6,741,892 B1 * | 5/2004 | Meadows et al. | 607/116 |
| 6,749,574 B2 | 6/2004 | O'Keefe | |
| 6,776,668 B1 | 8/2004 | Scyoc et al. | |
| 7,134,919 B2 | 11/2006 | Putz | |
| 7,402,083 B2 * | 7/2008 | Kast et al. | 439/660 |
| 7,425,142 B1 | 9/2008 | Putz | |
| 7,647,111 B2 | 1/2010 | Ries et al. | |
| 7,769,458 B2 | 8/2010 | Ries et al. | |
| 2009/0132016 A1 | 5/2009 | Putz | |

* cited by examiner

*Primary Examiner* — Xuong Chung Trans
(74) *Attorney, Agent, or Firm* — Jansson Munger McKinley & Shape Ltd.

(57) ABSTRACT

An electrical connector for connecting a linear-array plural-contact tail of an in-body multi-contact medical electrode device. The connector includes an elongate body member defining an elongate void extending along the length of the body member. An array of electrical conductors are secured in the body member and project into the elongate void to facilitate electrical connection of the contacts on the tail when the plural-contact tail is in the elongate void. A cylindrical carrier member is rotatably contained in the elongate void, the carrier member itself forms a tail-receiving subvoid.

28 Claims, 12 Drawing Sheets

ELECTRICAL CONNECTOR FOR AN IN-BODY MULTI-CONTACT MEDICAL ELECTRODE DEVICE

FIELD

The field relates generally to electrical connectors used for monitoring and mapping of brain activity in patients with neurological disorders and, more particularly, to medical connectors and systems which facilitate accurate measurement for periods of time through the use of implanted devices and electrodes.

BACKGROUND

Accurate sensing of intracranial electrical activity, such as for determining epileptogenic foci or otherwise, often may require use of a plurality of brain contacts. Epileptogenic mapping is one example of the use of electrical devices with tissue-engagement contacts. Examples of two kinds of intracranial electrical contact devices are depth probes and flexible flat surface members.

Depth probes, which may be referred to as "depth electrodes," penetrate deep into the brain tissue. On the other hand, flexible flat surface members, including what are sometimes referred to as "strip" electrodes and "grid" electrodes, may be placed subdurally in direct contact with brain tissue at the surface of the brain.

Examples of such electrodes include but are not limited to electrodes described in U.S. Pat. No. 4,735,208 (Wyler, et al.), U.S. Pat. No. 4,805,625 (Putz), U.S. Pat. No. 4,903,702 (Putz), U.S. Pat. No. 5,044,368 (Putz), and U.S. Pat. No. 5,097,835 (Putz).

Each of these different kinds of intracranial tissue-engagement electrodes are connected to some circuitry which typically captures and records the EEG signals for analysis of various types. There is a diagnostic need for an increased number of electrodes in order to increase the precision of analysis and diagnosis based on the captured EEG information. An increase in the number of electrodes requires higher data transmission bandwidths if the full amount of data captured from the electrodes is delivered to the monitoring system electronics. Further, there is a diagnostic need to monitor patients for longer periods of time, again for increased precision of diagnosis.

Multi-contact medical electrode devices are placed in the human body for various purposes, such as brain-mapping in epilepsy treatment. In such treatments wires generally extend from the multi-contact medical electrode to a plural-contact tail. The plural-contact tail is linear in shape and contains an array of sleeve-like contacts spaced therealong. The plural contacts of the plural-contact tail are to facilitate quick electrical connection of the contacts of the multi-contact medical electrode device such as for monitoring, recording and analysis purposes. Connectors have been configured to simultaneously engage the contacts of the plural-contact tail for their individual electrical connection to separate wire strands which emerge from the connector.

Various connectors have been developed to facilitate plural-contact connection. Examples of such prior art plural-contact medical connectors are those disclosed in the following United States patents: U.S. Pat. No. 4,379,462 (Borkan, et al.), U.S. Pat. No. 4,461,304 (Kuperstein), U.S. Pat. No. 4,516,820 (Kuzma), U.S. Pat. No. 4,633,889 (Talalla, et al.) and U.S. Pat. No. 4,676,258 (Inokuchi, et al.), U.S. Pat. No. 4,712,557 (Harris), U.S. Pat. No. 4,744,371 (Harris), U.S. Pat. No. 4,850,359 (Putz), U.S. Pat. No. 4,869,255 (Putz), U.S. Pat. No. 5,560,358 (Arnold, et al.), U.S. Pat. No. 5,902,236 (Iversen), U.S. Pat. No. 6,415,168 (Putz), U.S. Pat. No. 6,575,759 (Ollivier) and U.S. Pat. No. 7,425,142 (Putz).

Some medical connectors of the prior art have a number of shortcomings. One concern in a surgical setting that involves much equipment, many wires and hoses and the like, is that the connector be small in size to facilitate easy operation by medical personnel. It would be advantageous to have a connector which is small and slim so that it can be easily maneuvered by medical personnel during surgery. A slim design is particularly advantageous with respect to connectors that have a great number of contacts. Some connectors in the prior art are large in size and clumsy making them difficult to organize and manage. Some connectors in the prior art consist of a two-piece design with portions that must open and close for insertion of a plural-contact tail. Such connectors can also be difficult to organize and manage.

Certain prior art connectors utilized a flat ribbon-type cable that emerged laterally off the top of the connector giving the connector a bulky appearance. Other prior art connectors had a large build-up of epoxy protruding along the top of the connector that also added bulk.

When using a medical connector it is important that a constant and reliable electrical connection be present so that accurate information can be obtained. Some connectors in the prior art may create concerns with reliability of the connection. A reliable electrical connection is also of paramount importance since often the connectors are in use for lengthy periods of time. If a connector fails during use all of the information obtained may be lost or rendered inaccurate.

Medical connectors for use in patients who have a seizure tendency must also be secure. If a patient has a seizure there is the chance that the electrical connections could be destroyed or disrupted. Specifically, the plural-contact tails of multi-contact electrodes can become dislodged or broken by the involuntary movements that occur during a seizure. Therefore, it is important that the connector be secure so that it can withstand the jerking motions that are characteristic of seizures.

In certain prior art devices the electrical connector is a connector of the type that does not provide a secure connection and therefore, the connector can become dislodged or broken. If a connector does become dislodged or broken it can result in a significant loss of information and time.

In summary, there are problems and shortcomings in the prior art connectors for use with multi-contact medical electrode devices.

OBJECTS OF THE INVENTION

It is an object of this invention to provide a connector for multi-contact medical electrode devices overcoming some of the problems and shortcomings associated with the prior art.

Another object is to provide a multi-contact medical connector which has a streamlined one-piece design that facilitates easy operation by medical personnel.

Another object is to provide a multi-contact medical connector which gives highly reliable and constant electrical connections.

Yet another object of the invention is to provide a multi-contact medical connector which is secure given the involuntary jerking motions which are customary with a seizure condition.

These and other objects of the invention will be apparent from the following descriptions and from the drawings.

SUMMARY

This device is an electrical connector for an in-body multi-contact medical electrode device which is used in combination with a linear-array plural-contact tail.

The multi-contact medical connector of this device is a connector of the type that includes an elongate body member having proximal and distal ends and defining an elongate void extending along the length of the body member, an array of electrical conductors secured in the body member and projecting into the elongate void to facilitate electrical connection of the contacts on the tail when the plural-contact tail is in the elongate void. The multi-contact medical connector further includes a cylindrical carrier member rotatably contained in the elongate void, the carrier member itself forming a tail-receiving subvoid exposed along the outer surface of the carrier member to expose the contacts to engagement by the array of electrical conductors in the elongate void when the carrier member is rotated to bring the tail-containing subvoid into registry with the electrical conductors.

It is highly preferred that the carrier member includes outer-surface notches adjoining the subvoid to more fully expose the contacts of the tail at the outer surface of the carrier member. It is also highly preferred that the carrier member includes a finger tab secured to the carrier member and extending through an opening in the body member to facilitate pivoting of the carrier member between tail insertion and tail connection positions. Preferably, the carrier member is held in the tail connection position through frictional engagement between the finger tab and body member.

In some highly preferred embodiments the body member includes a detent which contacts the finger tab through frictional engagement and holds the connector in a locked position. In some embodiments, the electrical conductors are spring-loaded pin plunger devices. Preferably, the spring-loaded pin plunger devices on the body member extend from a presentation surface at an angle substantially perpendicular to the outer surface of the carrier member. In some embodiments, the spring-loaded pin plunger devices project at least halfway across and into the subvoid of the carrier member when the plural-contact tail is not in place.

In highly preferred embodiments of the inventive multi-contact medical connector, the connector includes end caps for snap-engagement with the proximal and distal ends of the body member. Preferably, the proximal end cap includes an arcuate slot having a radial cross dimension approximating the diameter of the subvoid, such that the plural-contact tail moves along the arcuate void when the carrier member pivots between tail insertion and tail connection positions. It is also preferred that the distal end cap on the body member includes an opening through which a multi-wire electrical cable extends to allow connection of individual wires to the electrical conductors In some preferred embodiments, the body member has a pair of opposed sidewalls and an edge therebetween forming a channel therealong receiving such wires, the wires and attachments thereof to the electrical conductors being sealed in the channel by a body of epoxy-like substance therealong.

Preferably, ribs are integrally formed with the opposed sidewalls and an elongate aperture is formed on each end cap. The ribs and apertures interact through frictional engagement thereby securing the end caps onto the body member.

The medical connector of this invention has significant advantages over connectors of the prior art. The connector is a streamlined one-piece design that facilitates easy operation by medical personnel. The medical connector of this invention is very easy to use in that it can be opened and closed with one hand. The connector provides excellent electrical connections and is secure. The connector also has improved electrical contacts between contacts of the plural-contact tail and the conductors of the connector device.

The invention includes the medical connector as described above, and also includes the combination of such a connector with the linear-array plural-contact tails of a multi-contact medical electrode. In highly preferred embodiments, the plural contacts of the plural-contact tail are annular sleeves having necked-in (e.g., crimped) ends. This configuration of plural-contact tail with the medical connector of this invention with its spring-loaded pin plungers allows quick withdrawal of the plural-contact tail without destruction of the plural-contact tail.

This advantage is significant in that it minimizes or prevents the problems which can occur if a patient's seizure causes violent jerking and yanking movements during e.g., a brain-mapping session. Such activity can result in the need for an expensive and time-consuming reorganization and reassembly of electrical components in order to allow resumption of the intended medical activity.

As used herein, the term "outer surface of the carrier member" as applied to the medical connector of this invention is the surface of the carrier member which is farthest from the middle or central part of the carrier member. For an illustration of the outer surface of the carrier member refer to FIGS. 9-10.

Other objects, advantages and features will become apparent from the following specification when taken in conjunction with the accompanying drawings.

BRIEF. DESCRIPTION OF THE DRAWINGS

The invention may be understood by reference to the following description taken in conjunction with the accompanying drawings, in which like reference numerals identify like elements. The drawings are not necessarily to scale, emphasis instead being placed upon illustrating the principles of the invention. In the accompanying drawings.

Figure 1:
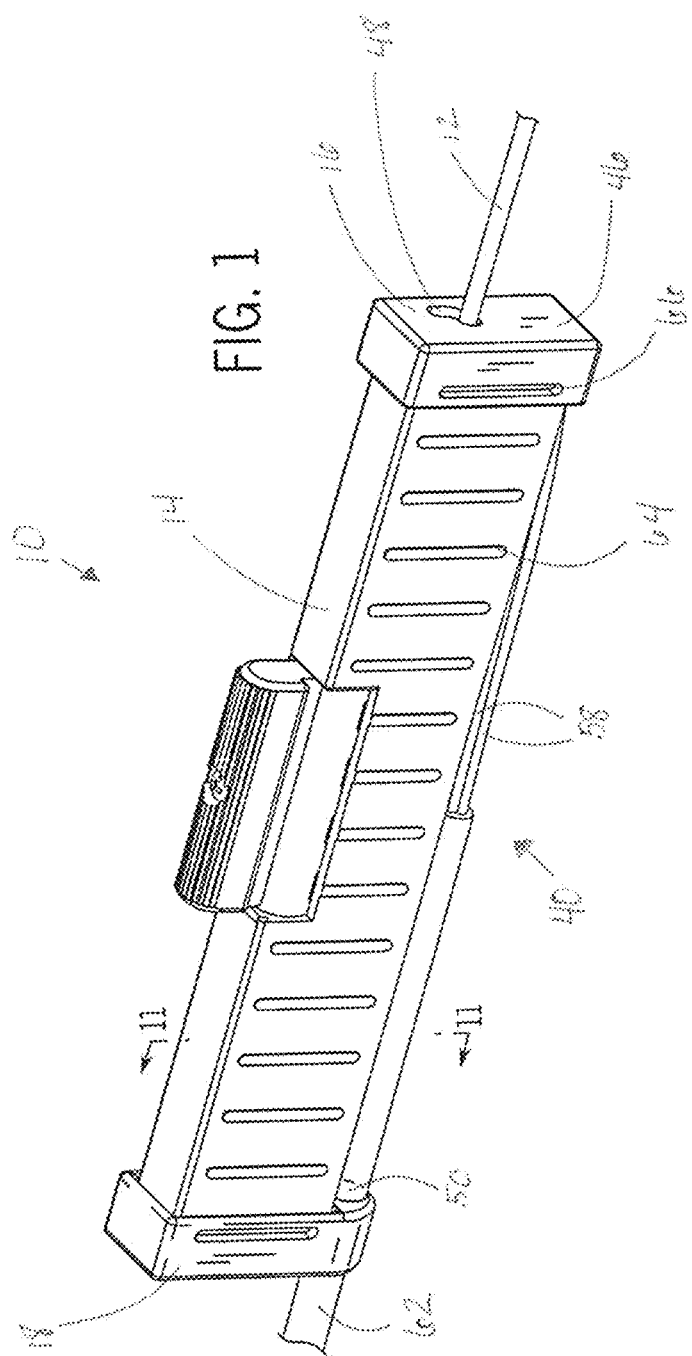
FIG. 1 is a perspective view of the connector in a closed or locked position, with the plural-contact tail of an in-body medical electrode positioned in the connector.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to coverall modifications, equivalents, and alternatives falling within the spirit and scope of the invention as defined by the appended claims.

DETAILED DESCRIPTION

While the present invention may be embodied in any of several different forms, the present invention is described herewith the understanding that the present disclosure is to be considered as setting forth an exemplification of the present invention that is not intended to limit the invention to the specific embodiment(s) illustrated. Nothing in this application is considered critical or essential to the present invention unless explicitly indicated as being "critical" or "essential."

FIGS. 1-12 illustrate an electrical connector 10 for connecting the linear-array plural-contact tail 12 of an in-body multi-contact medical electrode 11 (the in-body portion of which is not shown), having an array of electrical conductors 22 spaced therealong, each electrically linked by a small electrical wire running up and beyond tail 12 to a particular in-body contact on the in-body portion of the electrode 11. Connector 10 includes an elongate body member 14 which has an elongate void 20 extending along the length of body member 14.

Figure 8:
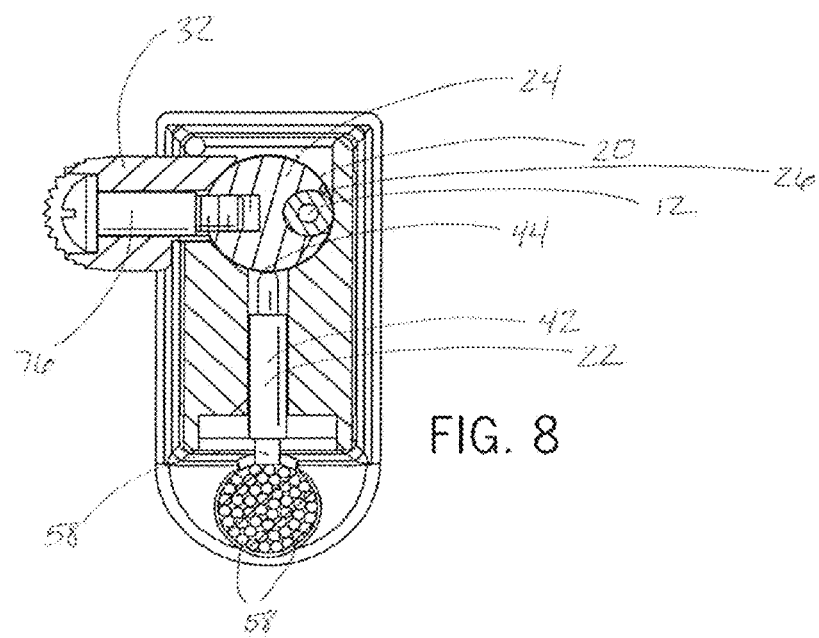
FIG. 8 is a cutaway view of the connector of FIG. 1, with the tail inserted illustrating certain internal details.
Figure 9:
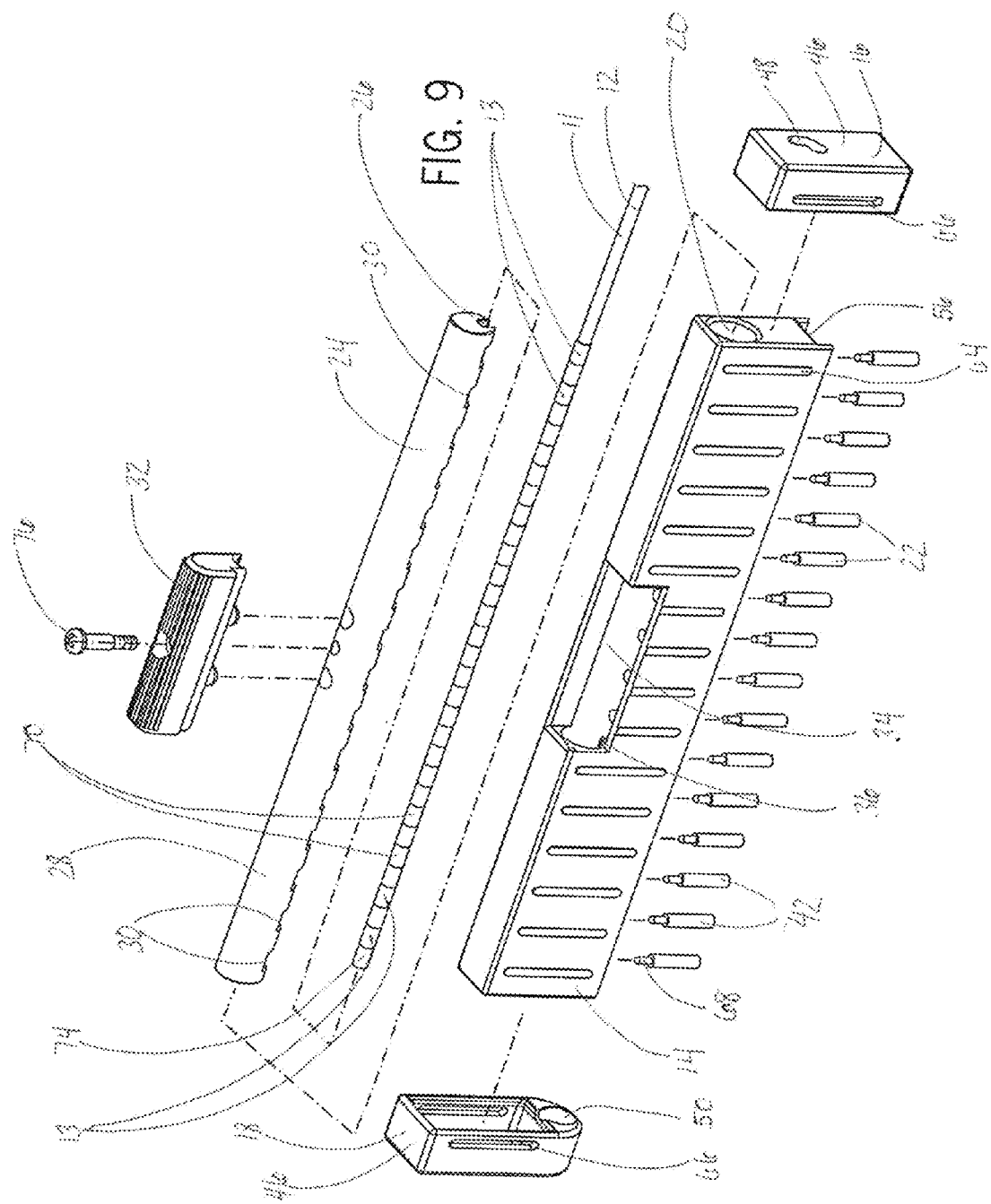
FIG. 9 is an exploded view of the connector of FIG. 1.

An array of electrical conductors 22 are secured in body member 14 and project into elongate void 20 to facilitate electrical connection of the contacts 13 on the tail 12 when plural-contact tail 12 is in the elongate void 20 as seen in FIGS. 8-9. Preferably, electrical conductors 22 are configured in a linear array as seen in FIG. 9. As shown in FIGS. 1-11, connector 10 includes a cylindrical carrier member 24 rotatably contained in elongate void 20. Carrier member 24 itself forms a tail-receiving subvoid 26 which is exposed along the outer surface 28 of carrier member 24 (see FIGS. 9 and 10). As illustrated in FIGS. 5 and 11, and best in FIG. 12, subvoid 26 exposes contacts 13 to engagement by the array of electrical conductors 22 in elongate void 20 when carrier member 24 is rotated to bring the tail containing subvoid 26 into registry with the electrical conductors 22.

Figure 2:
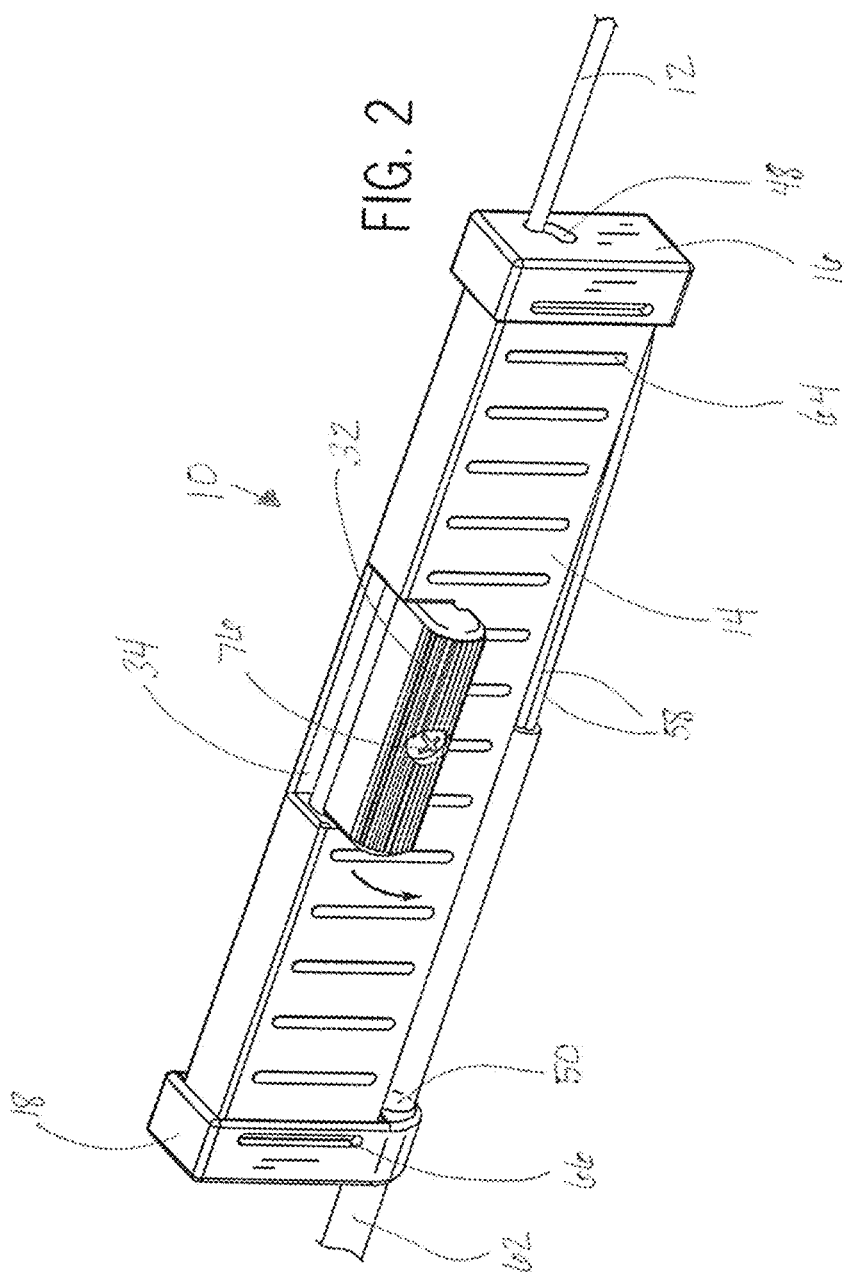
FIG. 2 is a perspective view of the connector of FIG. 1, with the connector in the open or unlocked position.
Figure 10:
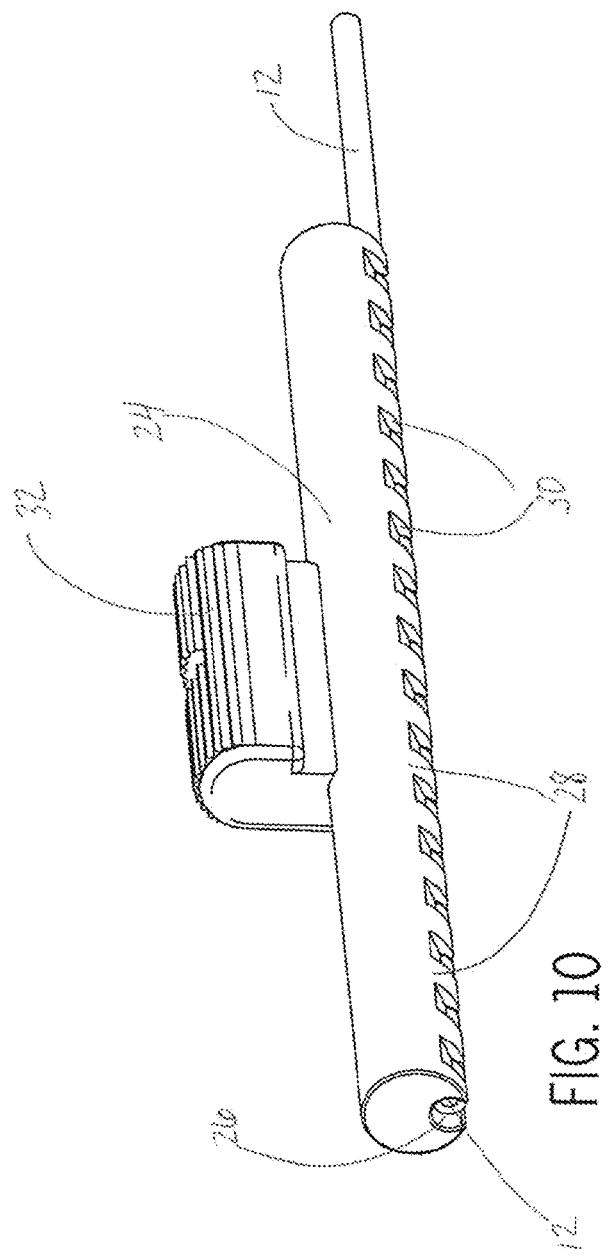
FIG. 10 is a perspective view of the cylindrical carrier member of the connector of FIG. 1 with the tail inserted.
Figure 11:
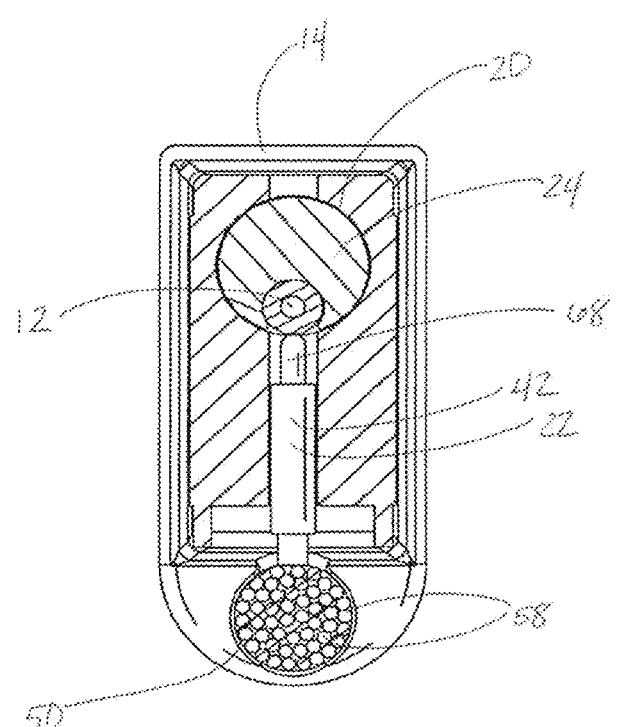
FIG. 11 is a cutaway view of the connector of FIG. 1, with the tail inserted illustrating certain internal details.

FIGS. 9 and 10 illustrate that carrier member 24 includes outer-surface notches 30 adjoining subvoid 26 to more fully expose the contacts 13 of the tail 12 at the outer surface 28 of carrier member 24. Carrier member 24 includes a finger tab 32 secured to carrier member 24 and extending through an opening 34 in body member 14 to facilitate pivoting of carrier member 24 between tail insertion and tail connection positions as seen in FIGS. 1, 2 and 9. Finger tab 32 can be secured to carrier member by screw 76 as seen in FIGS. 1 and 2 or by other various securement options.

Carrier member 24 is held in the tail connection position (or the closed/locked position 40, sec FIG. 1) through frictional engagement between the finger tab 32 and body member 14. As seen in FIG. 9, body member 14 includes a detent 36 which contacts the finger tab 32 through frictional engagement and holds connector 10 in a locked position 40.

Numerous types of electrical conductors 22 can be used with connector 10. One such type of electrical conductor 22 are spring-loaded pin plunger devices 42 as illustrated in FIGS. 5, 8-9 and 11. Electrical conductors 22 such as spring-loaded ball plungers or the like may also be used.

In the tail engagement position (see FIGS. 5 and 11), contacts 13 on tail 12 are placed into engagement with spring-loaded pin plunger devices 42 (or other type of electrical conductor), each plunger device 42 is electrically connected to one of the wires 58 which make-up the multi-wire electrical cable 62 which extends from the distal end 18 of body member 14 and which allows easy connection by means not shown with other equipment as seen in FIGS. 3, 5, 8 and 11.

FIG. 5 illustrates that spring-loaded pin plunger devices 42 on body member 14 extend from a presentation surface 44 at an angle substantially perpendicular to the outer surface 28 of carrier member 24. Spring-loaded pin plunger devices 42 project at least halfway across and into the subvoid 26 of carrier member 24 when plural-contact tail 12 is not in place (the tail insertion position also referred to as the open/unlocked position, see FIG. 2) as shown in FIG. 8. In the tail-connection position, carrier member 24 positions electrode tail 12 such that spring-loaded pin plungers 42 are just beyond-center with respect to the plural contacts 13 of tail 12, thereby providing reliable electrical contact and helping to maintain the tail connection position.

Notches 30 allow free rotation of carrier member 24 when tail 12 is not in place. (Not shown). As illustrated in FIGS. 9-12, notches 30 also serve the function of placing the plural contacts 13 of tail 12 into connection with pin plungers 42 or other electrical connector. As shown best in FIGS. 9 and 10, notches 30 are located on carrier member 24. Each notch 30 provides a lateral opening 34 to receive spring-loaded pin plunger devices 42 as carrier member 24 is pivoted to the tail connection position (closed/locked position 40).

Figure 3:
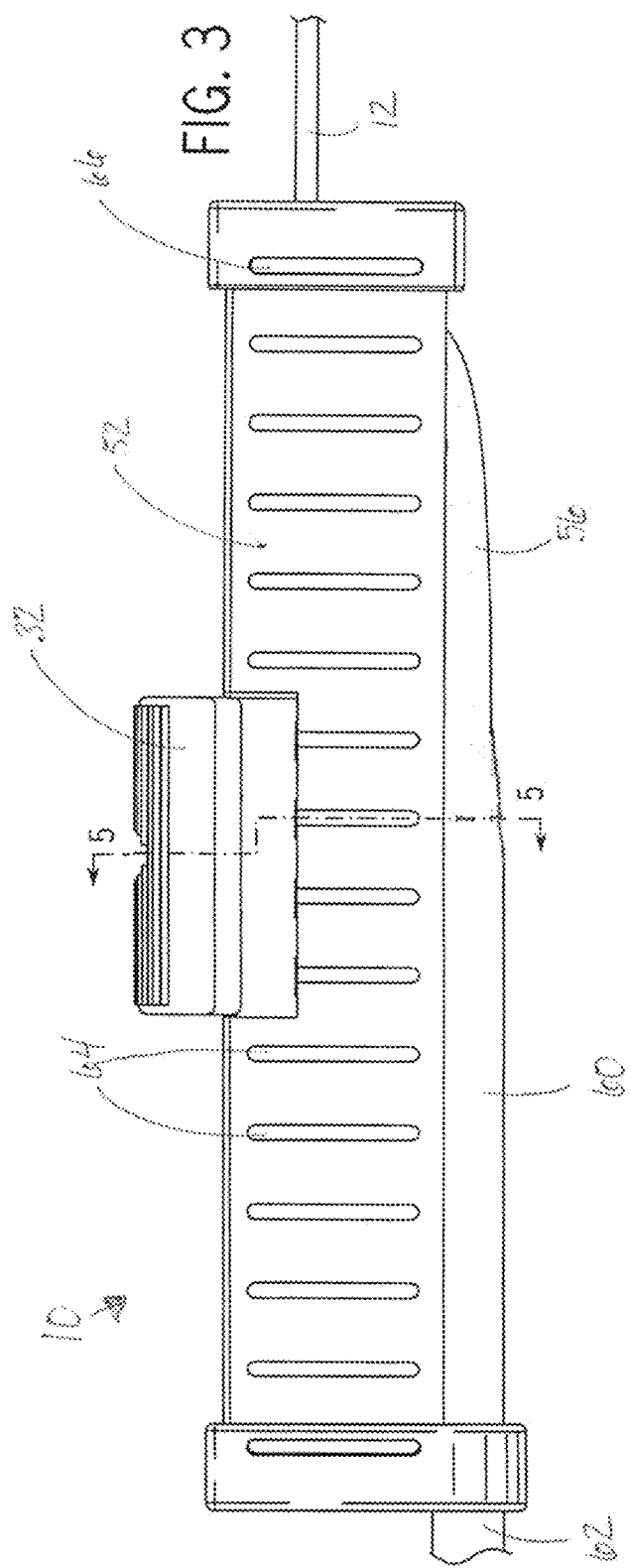
FIG. 3 is a front elevation of the connector of FIG. 1, with the channel and the body of epoxy-like substance.

Spring-loaded pin plunger devices 42 extend through elongate body member 14 to allow electrical connection with wires 58 as illustrated in FIG. 11. Spring-loaded pin plunger devices 42 are potted in their positions and protrude beyond presentation surface 44 (sec FIGS. 11 and 12). As shown in FIG. 3, wires 58 which make-up the multi-wire electrical cable 62 extend into channel 56 filled with an epoxy-like substance 60.

Body member 14 has proximal 16 and distal 18 ends as seen in FIGS. 1-3 and 6. FIG. 9, illustrates that subvoid 26 in carrier member 24 extends from an opening 34 at proximal end 16 to a stop (not shown) near distal end. The position of stop is fixed such that full insertion of tail 12 into subvoid 26 causes contacts 13 to be aligned with notches 30 along presentation surface 44 of body member 14 as seen in FIGS. 5 and 9-10. Subvoid 26 is configured to accommodate the presence of electrode tail 12 during tail insertion and tail connection positions as seen in the FIGURES.

Figure 4:
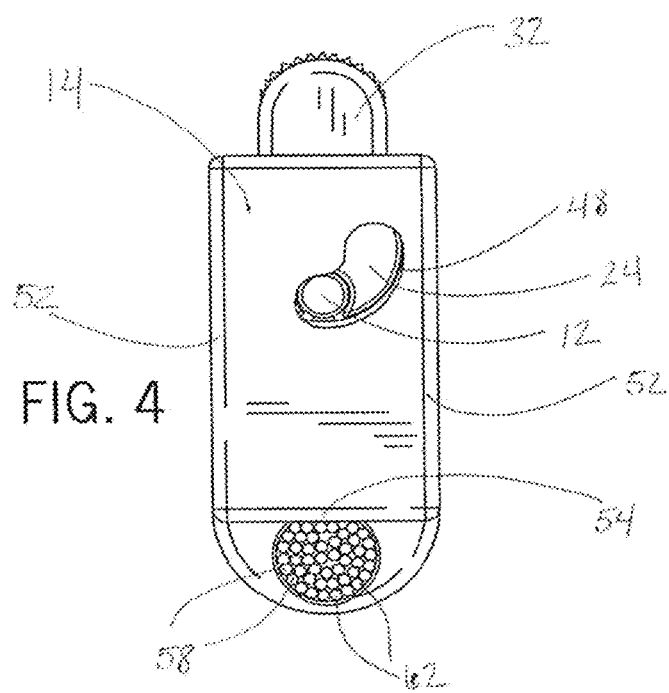
FIG. 4 is a right side elevation of the connector of FIG. 1, with the tail inserted and the connector in the closed or locked position.
Figure 5:
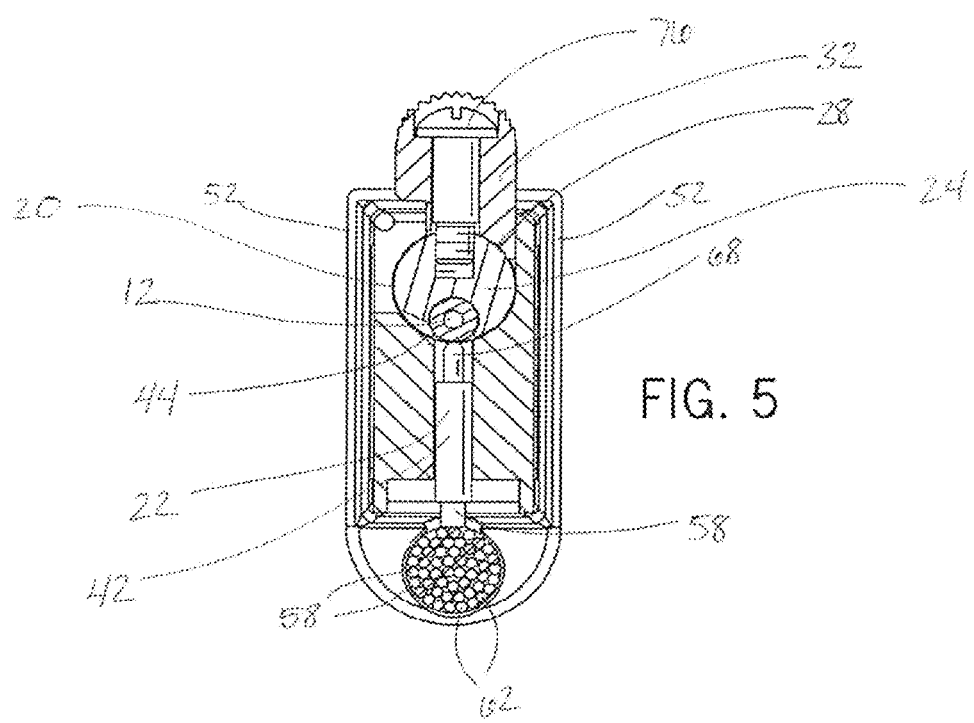
FIG. 5 is a cutaway view of the connector of FIG. 1, with the tail inserted illustrating certain internal details.
Figure 6:
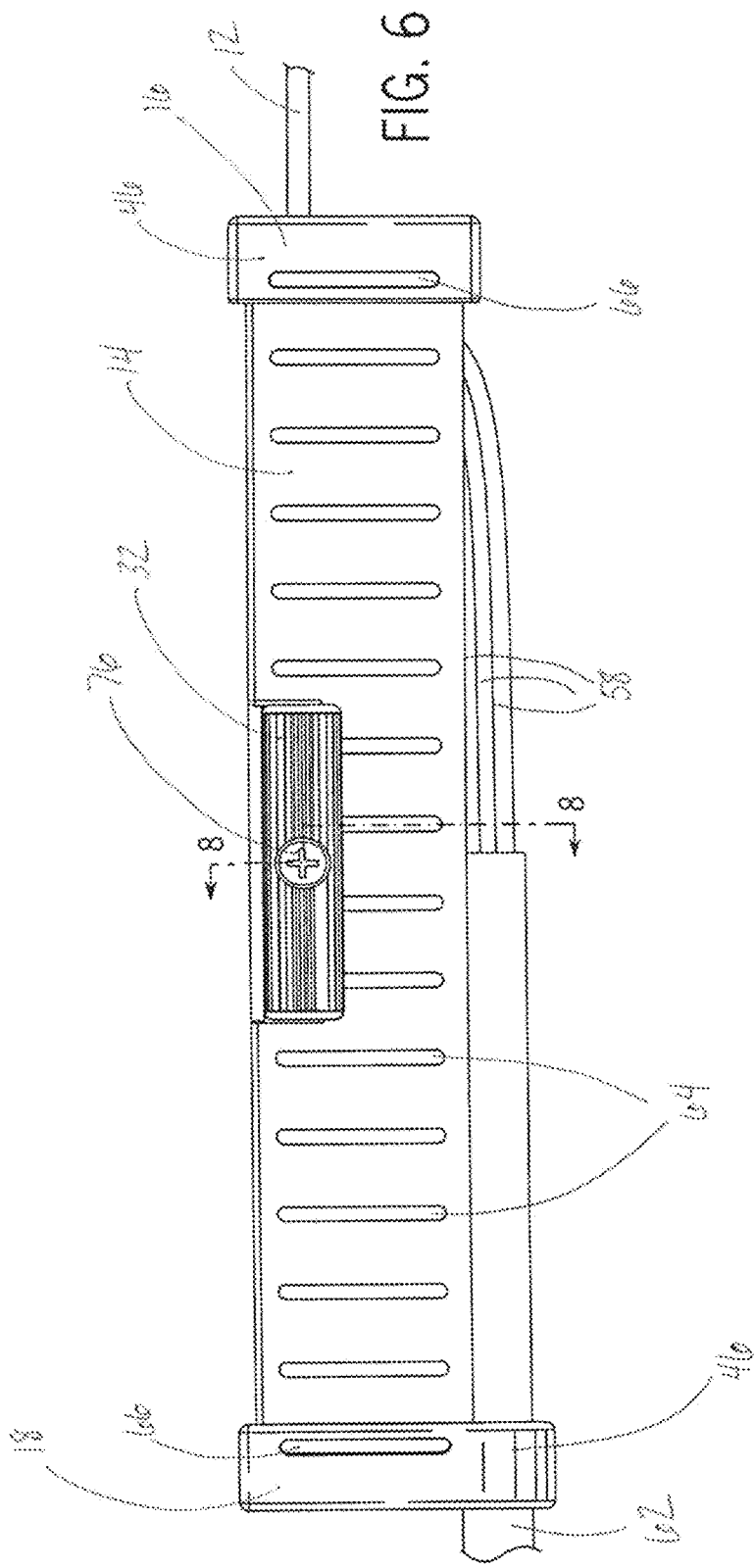
FIG. 6 is a front elevation of the connector of FIG. 1, with the tail inserted and the connector in the open or unlocked position.
Figure 7:
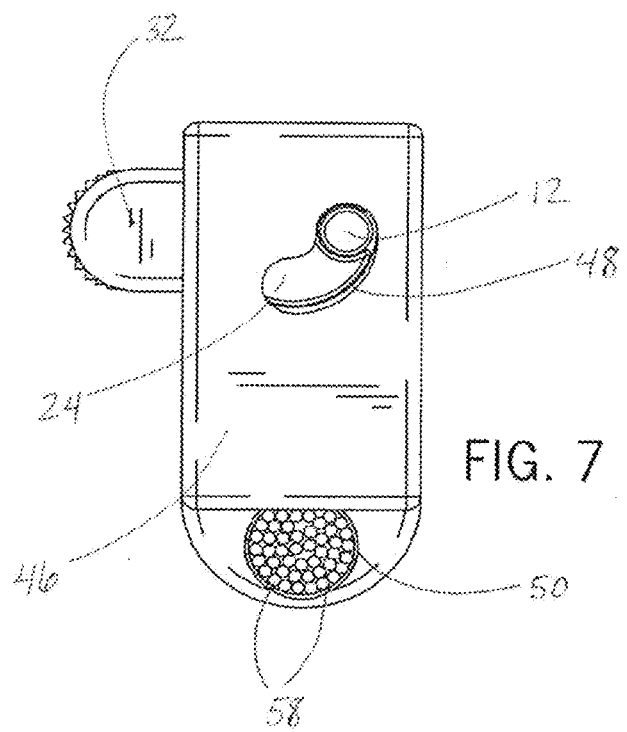
FIG. 7 is a right side elevation of the connector of FIG. 1, with the tail inserted and the connector in the open or unlocked position.

FIGS. 1-4, 6 and 9 illustrate that connector 10 includes end caps 46 for snap-engagement with the proximal 16 and distal 18 ends of body member 14. As seen in FIGS. 1-2, 4, 7 and 9, end cap 46 on the proximal end 16 of body member 14 includes an arcuate slot 48 having a radial cross dimension approximating the diameter oldie subvoid 26, such that the plural-contact tail 12 moves along arcuate slot 48 when carrier member 24 pivots between tail insertion and tail connection positions. Arcuate slot 48 has a greater cross dimension at the tail, insertion position than at the tail connection position as can be seen in FIG. 4. Therefore, mechanical engagement of the tail 12 with arcuate slot 48 in the tail connection position facilitates holding tail 12 in engagement with the connector 10. Frictional engagement between tail 12 and arcuate slot 48 facilitates holding of tail 12 in the engagement position. Distal end 18 of body member 14 includes an opening 50 through which multi-wire electrical cable 62 extends to allow connection of individual wires 58 to electrical conductors 22 as seen in FIGS. 1-3, 5-6, 8 and 11.

FIGS. 3-5 show that body member 14 has a pair of opposed sidewalls 52 and an edge 54 which forms a channel 56 which receives wires 58. Wires 58 and attachments (not shown) to electrical conductors 22 are sealed in channel 56 by a body of epoxy-like substance 60 as illustrated in FIGS. 3, 5 and 8. As seen in FIG. 3, channel 56 is defined by pair of opposed sidewalls 52 and edge 54. Channel 56 is about or equal to the length of body member 14.

Body member 14 also includes ribs 64 which are integrally formed with opposed sidewalls 52 as illustrated in FIGS. 1-2, 6 and 9. Each of the end caps 46, has an elongate aperture 66 which interacts with a single rib 64 on each sidewall 52. The interaction between each aperture 66 and rib 64 acts to hold each end cap 46 on body member 14 through frictional engagement (see FIGS. 1-3, 6 and 9). No adhesive is needed to assemble the connector 10 of this application. Various adhesives however, could be utilized if desired.

FIG. 9 illustrates details of contacts 13 and their relationship to pin portion 68 of spring-loaded pin plunger devices 42. Each contact 13 of plural-contact tail 12 is an annular sleeve which includes necked-in ends 70, formed by crimping. The outer diameter of contacts 13 are slightly greater than the outer diameter of the adjacent support tube 74 along which contacts 13 are mounted (not shown).

Figure 12:
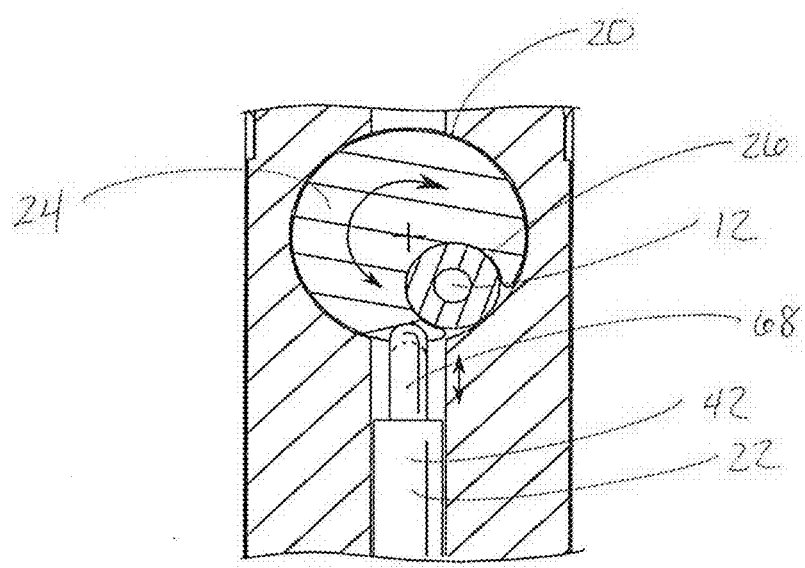
FIG. 12 is a cutaway view of the connector of FIG. 1, with the tail inserted illustrating the movement of the cylindrical carrier member.

FIG. 12 illustrates the rotation of carrier member 24 in body member 14. FIG. 12 also illustrates the up and down movement of electrical conductors.

Body member 14 of medical connector 10 may be made of hard plastic materials, a wide choice of which is available and will be apparent to those receiving this disclosure. Body member 14 is preferably made of opaque material. However, body member 14 could also be made of translucent or transparent material so that the positions of contacts 13 can be seen without looking at notches 30. A wide variety of materials is available for the various parts discussed and illustrated herein.

While the principles of this device have been described in connection with specific embodiments, it should be understood clearly that these descriptions are made only by way of example and are not intended to limit the scope of the device.

The invention claimed is:

1. In an electrical connector for connecting a linear-array plural-contact tail of an in-body multi-contact medical electrode device, the connector including an elongate body member having proximal and distal ends and defining an elongate void extending along the length of the body member, an array of electrical conductors secured in the body member and projecting into the elongate void to facilitate electrical connection of the contacts on the tail when the plural-contact tail is in the elongate void, the improvement comprising a cylindrical carrier member rotatably contained in the elongate void, the carrier member itself forming a tail-receiving subvoid exposed along the outer surface of the carrier member to expose the contacts to engagement by the array of electrical conductors in the elongate void when the carrier member is rotated to bring the tail-containing subvoid into registry with the electrical conductors, the carrier member including outer-surface notches adjoining the subvoid to more fully expose the contacts of the tail at the outer surface of the carrier member.

2. The multi-contact medical connector of claim 1 wherein the carrier member includes a finger tab secured to the carrier member and extending through an opening in the body member to facilitate pivoting of the carrier member between tail insertion and tail connection positions.

3. The multi-contact medical connector of claim 2 wherein the carrier member is held in the tail connection position through frictional engagement between the finger tab and body member.

4. The multi-contact medical connector of claim 3 wherein the body member includes a detent which contacts the finger tab through frictional engagement and holds the connector in a locked position.

5. The multi-contact medical connector of claim 1 wherein the electrical conductors are spring-loaded pin plunger devices.

6. The multi-contact medical connector of claim 5 wherein the spring-loaded pin plunger devices on the body member extend from a presentation surface at an angle substantially perpendicular to the outer surface of the carrier member.

7. The multi-contact medical connector of claim 6 wherein the spring-loaded pin plunger devices project at least halfway across and into the subvoid of the carrier member when the plural-contact tail is not in place.

8. The multi-contact medical connector of claim 5 wherein at the tail-connection position the carrier member positions the electrode tail such that the spring-loaded pin plungers are just beyond-center with respect to the plural contacts of the tail, thereby providing reliable electrical contact and helping to maintain the tail connection position.

9. The multi-contact medical connector of claim 1 further including an end caps for snap-engagement with the proximal and distal ends of the body member.

10. The multi-contact medical connector of claim 9 wherein the proximal end cap includes an arcuate slot having a radial cross dimension approximating the diameter of the subvoid, such that the plural-contact tail moves along the arcuate slot when the carrier member pivots between tail insertion and tail connection positions.

11. The multi-contact medical connector of claim 10 wherein the arcuate slot has a greater cross dimension at the tail insertion position than at the tail connection position, whereby mechanical engagement of the tail with the slot in the tail connection position facilitates holding the tail in engagement with the connector.

12. The multi-contact medical connector of claim 1 wherein the distal end of the body member includes an opening through which a multi-wire electrical cable extends to allow connection of individual wires to the electrical conductors.

13. The multi-contact medical connector of claim 12 wherein the body member has a pair of opposed sidewalls and an edge therebetween forming a channel therealong receiving such wires, the wires and attachments thereof to the electrical conductors being sealed in the channel by a body of epoxy-like substance therealong.

14. The multi-contact medical connector of claim 13 further including:
ribs integrally-formed with the opposed sidewalls; and
elongate apertures formed on each end cap;
whereby the end caps are held on the body member through frictional engagement between the ribs and apertures.

15. In combination, (a) an electrical connector comprising an elongate body member having proximal and distal ends and defining an elongate void extending along the length of the body member, an array of electrical conductors secured in the body member and projecting into the elongate void to facilitate electrical connection of the contacts on the tail when the plural-contact tail is in the elongate void; and (b) a linear-array plural-contact tail inserted within the elongate void, the improvement comprising a cylindrical carrier member rotatably contained in the elongate void, the carrier member itself forming a tail-receiving subvoid exposed along the outer surface of the carrier member to expose the contacts to engagement by the array of electrical conductors in the elongate void when the carrier member is rotated to bring the tail-containing subvoid into registry with the electrical conductors, the carrier member including outer-surface notches adjoining the subvoid to more fully expose the contacts of the tail at the outer surface of the carrier member.

16. The multi-contact medical connector of claim 15 wherein the carrier member includes a finger tab secured to the carrier member and extending through an opening in the body member to facilitate pivoting of the carrier member between tail insertion and tail connection positions.

17. The multi-contact medical connector of claim 16 wherein the carrier member is held in the tail connection position through frictional engagement between the finger tab and body member.

18. The multi-contact medical connector of claim 17 wherein the body member includes a detent which contacts the finger tab through frictional engagement and holds the connector in a locked position.

19. The multi-contact medical connector of claim 15 wherein the electrical conductors are spring-loaded pin plunger devices.

20. The multi-contact medical connector of claim 19 wherein the spring-loaded pin plunger devices on the body member extend from a presentation surface at an angle substantially perpendicular to the outer surface of the carrier member.

21. The multi-contact medical connector of claim 20 wherein the spring-loaded pin plunger devices project at least halfway across and into the subvoid of the carrier member when the plural-contact tail is not in place.

22. The multi-contact medical connector of claim 19 wherein at the tail-connection position the carrier member positions the electrode tail such that the spring-loaded pin plungers are just beyond-center with respect to the plural contacts of the tail, thereby providing reliable electrical contact and helping to maintain the tail connection position.

23. The multi-contact medical connector of claim 15 further including an end caps for snap-engagement with the proximal and distal ends of the body member.

24. The multi-contact medical connector of claim 22 wherein the proximal end cap includes an arcuate slot having a radial cross dimension approximating the diameter of the subvoid, such that the plural-contact tail moves along the arcuate slot when the carrier member pivots between tail insertion and tail connection positions.

25. The multi-contact medical connector of claim 24 wherein the arcuate slot has a greater cross dimension at the tail insertion position than at the tail connection position, whereby mechanical engagement of the tail with the slot in the tail connection position facilitates holding the tail in engagement with the connector.

26. The multi-contact medical connector of claim 15 wherein the distal end of the body member includes an opening through which a multi-wire electrical cable extends to allow connection of individual wires to the electrical conductors.

27. The multi-contact medical connector of claim 26 wherein the body member has a pair of opposed sidewalls and an edge therebetween forming a channel therealong receiving such wires, the wires and attachments thereof to the electrical conductors being sealed in the channel by a body of epoxy-like substance therealong.

28. The multi-contact medical connector of claim 27 further including:
   ribs integrally-formed with the opposed sidewalls; and
   elongate apertures formed on each end cap;
whereby the end caps are held on the body member through frictional engagement between the ribs and apertures.

* * * * *

UNITED STATES PATENT AND TRADEMARK OFFICE
CERTIFICATE OF CORRECTION

| | | |
|---|---|---|
| PATENT NO. | : 8,439,714 B2 | Page 1 of 1 |
| APPLICATION NO. | : 12/956729 | |
| DATED | : May 14, 2013 | |
| INVENTOR(S) | : Putz | |

It is certified that error appears in the above-identified patent and that said Letters Patent is hereby corrected as shown below:

In the Specification

Column 6, line 54, delete "oldie" and replace with --of the--.

Signed and Sealed this
Fourth Day of February, 2014

Michelle K. Lee
*Deputy Director of the United States Patent and Trademark Office*